US012465717B2

United States Patent
(12) United States Patent
Ratner

(10) Patent No.: US 12,465,717 B2
(45) Date of Patent: *Nov. 11, 2025

(54) BI-LEVEL POSITIVE AIRWAY PRESSURE DEVICE

(71) Applicant: MERCURY ENTERPRISES, INC., Clearwater, FL (US)

(72) Inventor: Jeffrey B. Ratner, Pinellas Park, FL (US)

(73) Assignee: MERCURY ENTERPRISES, INC., Clearwater, FL (US)

(*) Notice: Subject to any disclaimer, the term of this patent is extended or adjusted under 35 U.S.C. 154(b) by 724 days.

This patent is subject to a terminal disclaimer.

(21) Appl. No.: 17/877,889

(22) Filed: Jul. 30, 2022

(65) Prior Publication Data

US 2022/0362506 A1 Nov. 17, 2022

Related U.S. Application Data

(63) Continuation-in-part of application No. 16/752,718, filed on Jan. 27, 2020, now Pat. No. 11,433,194, which is a continuation-in-part of application No. 15/719,663, filed on Sep. 29, 2017, now Pat. No. 10,583,262, which is a continuation-in-part of application No. 14/853,079, filed on Sep. 14, 2015, now Pat. No. 10,258,759.

(60) Provisional application No. 62/050,554, filed on Sep. 15, 2014.

(51) Int. Cl.

| | |
|---|---|
| ***A61M 16/00*** | (2006.01) |
| ***A61M 16/08*** | (2006.01) |
| ***A61M 16/20*** | (2006.01) |

(52) U.S. Cl.

CPC ...... *A61M 16/206* (2014.02); *A61M 16/0096* (2013.01); *A61M 16/0858* (2014.02); *A61M 2016/0027* (2013.01)

(58) Field of Classification Search

CPC ............ A61M 16/206; A61M 16/0096; A61M 16/0858

See application file for complete search history.

(56) References Cited

U.S. PATENT DOCUMENTS

| | | | |
|---|---|---|---|
| 5,002,050 | A | 3/1991 | McGinnis |
| 5,438,980 | A | 8/1995 | Phillips |
| 5,896,857 | A | 4/1999 | Hely |
| 6,253,764 | B1 | 7/2001 | Calluaud |
| 8,316,845 | B2 | 11/2012 | Tappehorn |
| 8,439,036 | B2 | 5/2013 | Winter |
| 10,258,759 | B2 | 4/2019 | Ratner |

(Continued)

*Primary Examiner* — Margaret M Luarca

(74) *Attorney, Agent, or Firm* — Larson & Larson; Frank Liebenow; Justin P. Miller

(57) ABSTRACT

A bi-level positive airway pressure device includes a housing that has a patient port for connecting to an airway of a patient. There is a device (e.g., a nozzle) for generating a positive airway pressure that is directed through a conduit towards the patient port. An exhalation detector includes a nozzle emitting a jet of a gas directed across the conduit and directed at a receptor channel when exhalation gases flow from the patient port, thereby an increase a gas pressure is present at the receptor channel when the exhalation gases flow from the patient port. The exhalation detector converts the increase in the gas pressure into a movement of an occluding member such that when the exhalation gases flow from the patient port, the occluding member moves to block the means for generating the positive airway pressure.

14 Claims, 15 Drawing Sheets

(56) References Cited

U.S. PATENT DOCUMENTS

| | | | |
|---|---|---|---|
| 2014/0150793 | A1 | 6/2014 | Douglas et al. |
| 2016/0074607 | A1 | 3/2016 | Ratner |
| 2017/0232224 | A1 | 8/2017 | Ratner |
| 2018/0021532 | A1 | 1/2018 | Ratner |

BI-LEVEL POSITIVE AIRWAY PRESSURE DEVICE

CROSS-REFERENCE TO RELATED APPLICATION

This application is a continuation-in-part of U.S. patent application Ser. No. 16/752,718 filed Jan. 27, 2020; which, in turn, is a continuation-in-part of U.S. patent application Ser. No. 15/719,663 filed Sep. 27, 2017, now U.S. Pat. No. 10,583,262 issued Mar. 10, 2020; which, in turn, is a continuation-in-part of U.S. patent application Ser. No. 14/853,079 filed Sep. 14, 2015, now U.S. Pat. No. 10,258,759 issued Apr. 16, 2019, which in turn claims the benefit of U.S. provisional application No. 62/050,554 filed on Sep. 15, 2014, the disclosure of both are incorporated by reference.

FIELD

This invention relates to the field of fluids and more particularly to an apparatus for detecting airflow.

BACKGROUND

There are many instances when an indication of a flow rate of a gas needs to be determined. For example, in patients (e.g., mammals such as humans) that have respiratory issues such as chronic obstructive pulmonary disease (COPD), sleep apnea, etc., it is often required to provide assistance in filling their lungs with air, or inhalation. There exist devices that are interfaced to a patient's airway for providing such assistance by injecting a positive airway pressure towards and into the patient' airway, thereby assisting that patient with inhalation. In such devices, it is sometimes needed to determine when the patient is inhaling or exhaling, based upon the flow rate and direction of flow in such devices that are interfaced to the patient.

One type of device for providing such assistance is a Continuous Positive Airway Pressure (CPAP) device as described in, for example, U.S. Pat. No. 4,944,310. Continuous Positive Airway Pressure devices generally provide a gas pressure that is slightly greater than ambient air pressure into the patient's airway. Continuous Positive Airway Pressure devices work well for certain patients, but patients that have poor lung capability often find it harder to exhale due to the constant added pressure directed into the patient's air passages by the Continuous Positive Airway Pressure device. This is because the Continuous Positive Airway Pressure device continues to provide positive air pressure, even while the patient is exhaling.

Bi-level Positive Airway Pressure devices address this issue of exhalation as described above by detecting when the patient is exhaling and reducing the positive airway pressure until the patient completes exhalation and starts inhalation. In such, there are two different positive airway pressures delivered (hence bi-level), a higher positive airway pressure while the patient inhales and a lower positive airway pressure (e.g., atmospheric pressure) while the patient exhales.

To accomplish the bi-level positive airway pressure delivery, Bi-level Positive Airway Pressure devices of current have electrical transducers that senses when the patient is exhaling and an electrical circuit that receives an electrical signal from the transducers and responsive to that signal, modulates the positive airway pressure between two values. For example, U.S. Pat. Pub. 20140150793 describes such a Bi-level Positive Airway Pressure device that has a flow sensor connected to a controller. This device has a blower for providing the positive airway pressure and upon detecting that a patient/user is exhaling, the controller sets the blower to operate at a lower speed (or off), thereby reducing the positive airway pressure until the patient stops exhaling, at which time the controller detects the end of the exhalation and restarts the blower.

The above-described Bi-level Positive Airway Pressure devices are known to function well, especially with patients that have very little lung capacity. Unfortunately, many such patients are not limited to bed rest and wish to be mobile. It is known to provide the pressure component for positive airway pressure by a portable device, typically portable Continuous Positive Airway Pressure (CPAP) devices. Such devices typically derive the pressure component for positive airway pressure from a small battery operated pump or through a compressed gas cylinder (e.g., air, oxygen, etc.). It is possible, especially if made small and light enough to be carried by the patient. The sensors, the connections to the sensors, and the added electronics make portability hard to accomplish, especially if a compressed gas tank is utilized. Further, the issues related to battery charge maintenance become an issue. Further, due to the electronic components, power supplies, etc., it is difficult to dispose of such a device, making single-use devices out of the question. Such devices are not envisioned as to be sold as disposable devices.

This being said, there are many medical as well as non-medical needs for detecting the flow of a gas such as air through a passage such as through a pipe or duct. Since there are many situations in which there is little impedance to such gas flow (e.g., in a heating/air conditioning duct system), gas pressure is not a good indication of flow or flow rates.

What is needed is a device that detects a gas flow through a conduit.

SUMMARY

In a first embodiment, a bi-level positive airway pressure device is disclosed including a housing that has a patient port for connecting to an airway of a patient. There is a device (e.g., a nozzle) for generating a positive airway pressure that is directed through a conduit towards the patient port. An exhalation detector includes a nozzle emitting a jet of a gas directed across the conduit and directed at a receptor channel when exhalation gases flow from the patient port, thereby an increase a gas pressure is present at the receptor channel when the exhalation gases flow from the patient port. The exhalation detector converts the increase in the gas pressure into a movement of an occluding member such that when the exhalation gases flow from the patient port, the occluding member moves to block the means for generating the positive airway pressure.

In another embodiment, bi-level positive airway pressure device includes a housing having a patient port for connecting to an airway of a patient and a source of positive airway pressure directed through the housing and towards the patient port. The source of the positive airway pressure is positioned near an end of the housing that is distal from the patient port. There is a nozzle emitting a jet of a gas directed across the housing at an end of the housing that is closest to the patient port. A first receptor positioned on a side of the housing opposite of the nozzle and receives the gas from the jet of the gas when there is absence of exhalation gases flowing from the patient port, thereby an increased gas pressure is present at the first receptor when there is an absence of the exhalation gases flowing from the patient port. A second receptor channel is positioned on the side of the housing opposite of the nozzle but closer to the source of the positive airway pressure than the first receptor such that the second receptor channel receives the gas from the jet of the gas when the exhalation gases flow from the patient port and through the housing, thereby the increased gas pressure is present in the second receptor channel during exhalation. A diaphragm seals a chamber into a first section and a second section, the diaphragm is mechanically interfaced to an occluding member; the first section of the chamber is fluidly interfaced to the first receptor and the second section fluidly of the chamber is fluidly interfaced to the second receptor such that in absence of the flow of the exhalation gases from the patient port, the increase in the gas pressure in the first section exerts force on a first side of the diaphragm to deform the diaphragm and move the occluding member away from the source of the positive airway pressure and when the exhalation gases flow from the patient port, the increase in the gas pressure in the second section exerts an opposing force on an opposite side of the diaphragm to deform the diaphragm and move the occluding member to cover the source of the positive airway pressure.

In another embodiment, bi-level positive airway pressure device includes a housing that has a patient port for connecting to an airway of a patient and a source of positive airway pressure directed through the housing and towards the patient port. The source of the positive airway pressure is positioned near an end of the housing that is distal from the patient port. A nozzle emits a jet of a gas directed across the housing at an end of the housing that is closest to the patient port. A first receptor is positioned on a side of the housing opposite of the nozzle, receiving the gas from the jet of the gas when there is absence of exhalation gases flowing from the patient port, thereby presenting an increased gas pressure at the first receptor when there is an absence of the exhalation gases flowing from the patient port. A second receptor is positioned on the side of the housing opposite of the nozzle but closer to the source of the positive airway pressure than the first receptor such that the second receptor receives the gas from the jet of the gas when the exhalation gases flow from the patient port and through the housing, thereby the increase in gas pressure is present in the second receptor during the exhalation. A piston within a cylinder is mechanically interfaced to an occluding member. A first side of the cylinder is fluidly interfaced to the first receptor and a second side of the cylinder is fluidly interfaced to the second receptor such that in absence of the flow of the exhalation gases from the patient port, the increase in the gas pressure on the first side of the cylinder exerts force on the first side of the piston to move the piston and, therefore, move the occluding member away from source of the positive airway pressure. Similarly, when the exhalation gases flow from the patient port, the increase in the gas pressure on the second side of the cylinder exerts an opposing force on the second side of the piston to move the piston and, therefore, move the occluding member to block the source of the positive airway pressure.

In another embodiment, a bi-level positive airway pressure device is disclosed including a housing that has a patient port for connecting to an airway of a patient. Within the housing is a device such as a nozzle that generates a positive airway pressure directed towards to patient port. Also within the housing is a subsystem that mechanically detects exhalation and/or inhalation (by the patient connected to the patient port) entering into the patient port. Responsive to sensing exhalation and/or inhalation, positive airway pressure is increased or decreased mechanically or pneumatically. For example, upon detecting exhalation, a blocking device occludes (moves in front of) the device that generates positive airway pressure. This reduces or stops the positive airway pressure until the subsystem no longer detects exhalation, at which time the blocking device is operated (moved away) to no longer occlude the device for generating positive airway pressure, thereby providing positive airway pressure to the patient port during, for example, inhalation.

In another embodiment, a bi-level positive airway pressure device is disclosed including a housing having a patient port for connecting to an airway of a patient. The bi-level positive airway pressure device has mechanisms for generating a positive airway pressure directed towards the patient port and mechanisms for detecting inhalation from the patient port or exhalation into the patient port. Mechanisms are provided for increasing or decreasing the positive airway pressure, decreasing the positive airway pressure when the mechanism for detecting inhalation/exhalation detects exhalation (e.g., the patient breaths out), increasing the positive airway pressure when the mechanism for detecting inhalation/exhalation detects inhalation (e.g., the patient breaths in), etc., thereby making it easier for the patient to exhale, etc.

In another embodiment, a bi-level positive airway pressure device is disclosed including a housing having a patient port for connecting to an airway of a patient. A nozzle generates a positive airway pressure directed towards the patient port. The nozzle is positioned near an end of the housing distal from the patient port. A mechanical device for detecting an inhalation and/or exhalation flow entering into or exiting from the patient port is coupled to a occluding member. Upon detection of exhalation, the mechanical device causes the occluding member to at least partially occlude the nozzle, thereby abating the positive airway pressure. Upon detection of inhalation, the mechanical/pneumatic device causes the occluding member to move to a position of less occlusion, thereby providing increased positive airway pressure.

In another embodiment, a bi-level positive airway pressure device is disclosed including a housing having a patient port at one end for interfacing to an airway of a patient. A nozzle that is interfaced to a supply of gas generates a positive airway pressure in a direction aimed at the patient port. The nozzle situated at an end of the housing distal from the patient port and the nozzle is directed towards the patient port. An occluding member is movably positioned between the nozzle and the patient port and is positionable in at least two positions. A first position at least partially blocks the positive airway pressure and a second position allows greater flow of the positive airway pressure to the patient port. A gas jet is initially aimed at a first port and during exhalation; the gas jet deflects to be aimed at a second port. The first port is in fluid communications with a first mechanical device that moves the occluding member to the second position when the first mechanical device (e.g., diaphragm) receives pressure from the gas jet, thereby enabling the positive airway pressure. The second port is in fluid communications with a second mechanical device that moves the occluding member to the first position when the second mechanical device (e.g., diaphragm) receives pressure from the gas jet, thereby abating the positive airway pressure when the exhalation flow is detected.

In another embodiment, a device for detecting a flow of a first gas in a conduit is disclosed including a gas jet interfaced to a side of the conduit. The gas jet emitting a jet of a second gas aimed across the conduit (it is anticipated that the first gas and second gas are the same or different).

A fluid port is interfaced to a distal side of the conduit for receiving the jet. A pressure detector for detecting pressure of the jet of the second gas is fluidly interfaced to the fluid port so that when a there is first rate of flow of the first gas within the conduit, the jet of the second gas deflects towards the fluid port and a first pressure is present at the pressure detector and when there is a second, different rate of flow of the first gas within the conduit. the jet of the second gas deflects away from the fluid port and a second pressure is present at the pressure detector. The second pressure is lower than the first pressure.

In another embodiment, a device for detecting a flow of a first gas in a conduit is disclosed including a gas jet interfaced to a side of the conduit. A fluid port is interfaced to a distal side of the conduit for receiving the jet of the second gas and a diaphragm is interfaced to the fluid port such that upon a first flow rate of the first gas within the conduit, the gas jet enters the fluid port and exerts a pressure on a first side of the diaphragm and moves the diaphragm in a first direction and upon a second flow rate of the first gas within the conduit, the gas jet is deflected away from the fluid port and the pressure decreases on the first side of the diaphragm and moves the diaphragm in a second direction opposite of the first direction.

In another embodiment, a device for detecting a flow of a first gas in a conduit is disclosed including a gas jet interfaced to a side of the conduit; the gas jet emitting a jet of a second gas aimed across the conduit. A first fluid port is interfaced to a distal side of the conduit for receiving the jet of the second gas in absence of the flow of the first gas. There is a second fluid port interfaced to the distal side of the conduit for receiving the jet of the second gas. The second fluid port receives the jet of the second gas when the jet of the second gas is deflected by the flow of the first gas in a first direction. A diaphragm is fluidly interfaced to the fluid port and a second, opposing side of the diaphragm fluidly interfaced to the second fluid port. In absence of the flow of the first gas, the diaphragm is moved in a first diaphragm direction by a pressure of the jet of the second gas entering the fluid port and in presence of the flow of the first gas, the diaphragm is moved in a second diaphragm direction by the pressure of the jet of the second gas entering the second fluid port; the second diaphragm direction being opposite the first diaphragm direction.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1A:
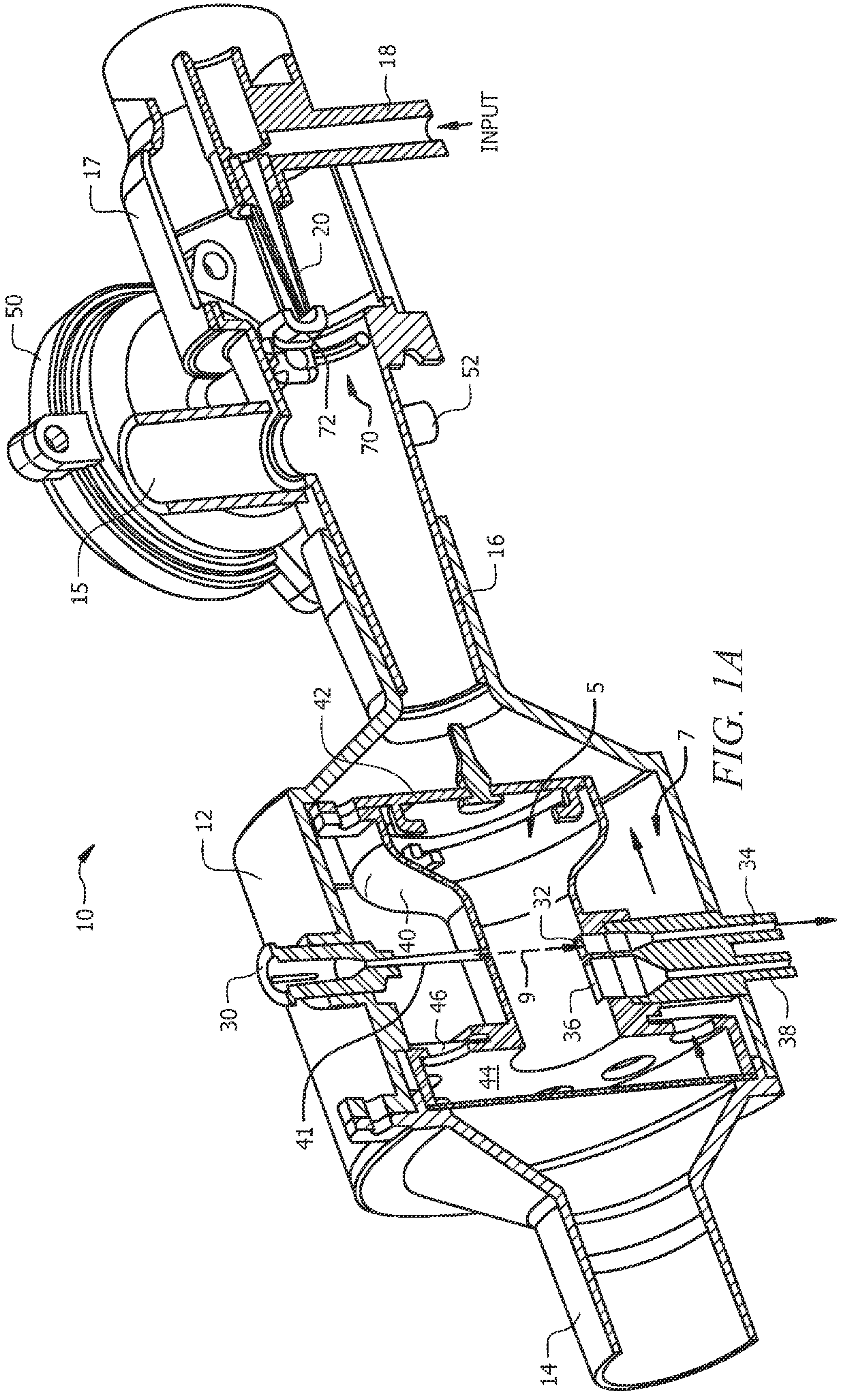
FIGS. 1A and 1B illustrate cut-away views of a mechanical bi-level positive airway pressure system.

Reference will now be made in detail to the presently preferred embodiments of the invention, examples of which are illustrated in the accompanying drawings. Throughout the following detailed description, the same reference numerals refer to the same elements in all figures.

Figure 1B:
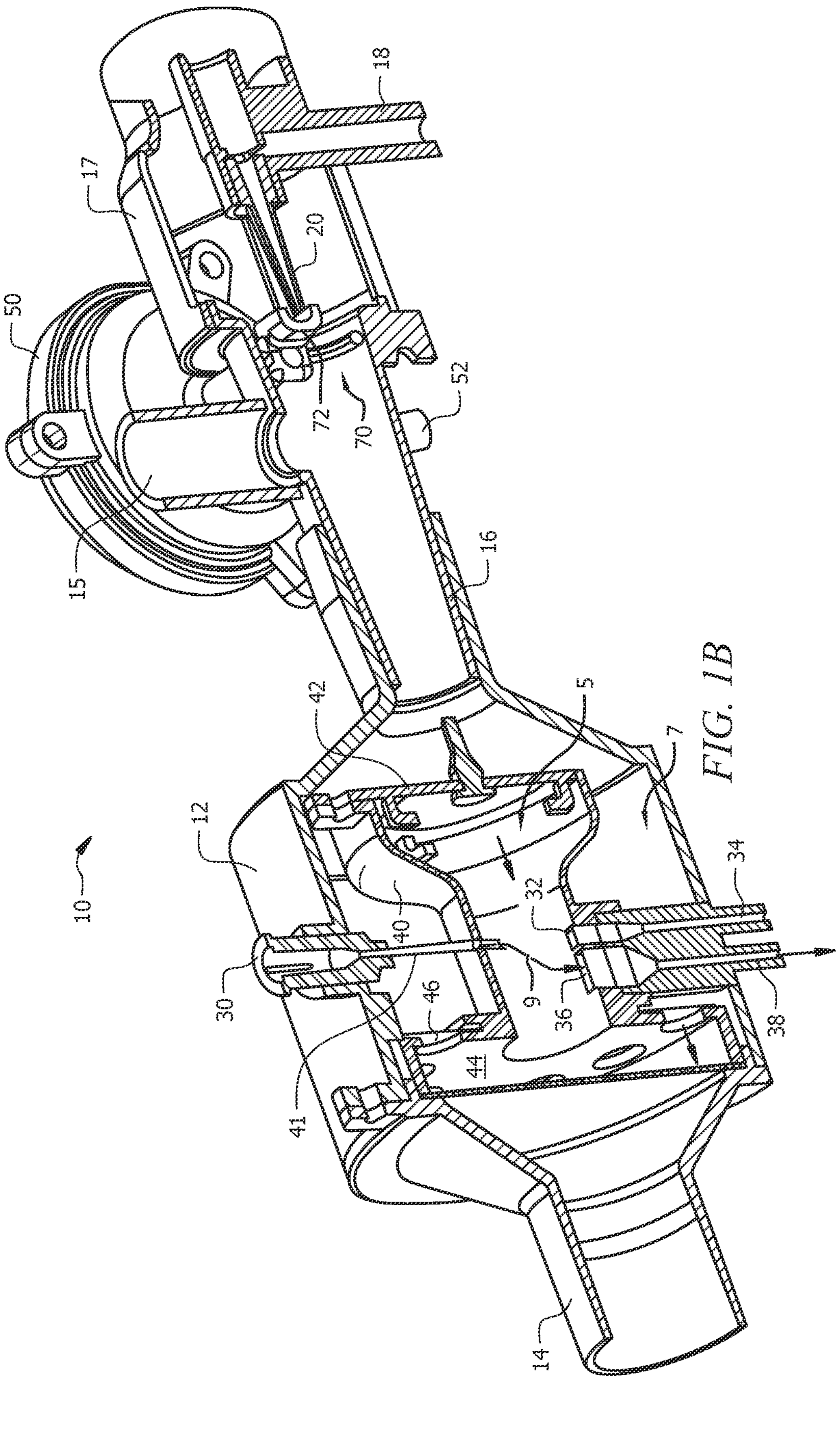

Referring to FIGS. 1A and 1B, cut-away views of a mechanical bi-level positive airway pressure system 10 are shown. The principles of operation of the bi-level positive airway pressure system 10 are understandable from FIGS. 1A and 1B.

In FIGS. 1A and 1B, the patient airway (not shown) is interfaced to the patient port 14 by any way known in the industry such as by a nasal cannula, facemask, endotracheal tube, etc.

As shown in FIG. 1A, during exhalation, the flow of air from the patient travels through the outer chamber 7 of the detection section 12 as indicated by the air flow arrow. A first one-way valve 44/46 allows flow in the exhalation direction through the outer chamber (indicated by an arrow) while a second one-way valve 40/42 precludes flow through the inner chamber 5 defined by an inner structure member of the second one-way valve 40/42.

As shown in FIG. 1B, during inhalation, the one-way valves 44/46/40/42 operate in an opposing fashion, in that, the flow of air from the positive pressure nozzle 20 (optionally along with atmospheric air) travels through the inner chamber 5 of the detection section 12 as indicated by the inhalation air flow arrow in FIG. 1B. The first one-way valve 44/46 blocks flow in the inhalation so there is no flow through the outer chamber 7 while the second one-way valve 40/42 allows flow through the inner chamber 5 as indicated by the inhalation flow arrow. The positive pressure nozzle 20 is provided with gas under pressure from a positive pressure input port 18.

In FIGS. 1A and 1B, there is a pressurized gas input 30 that is connected to a source a pressurized gas (e.g., air, oxygen, etc.—not shown). A jet 9 of gas flows out of a gas stream nozzle 41 and crosses the inner chamber 5 falling onto one of the receptor channels 32/36. As shown in FIG. 1A, when the patient is not inhaling (e.g., exhaling or at rest), the jet 9 of gas flows directly across the inner chamber 5 and into the first receptor channel 32. The first receptor channel 32 is fluidly interfaced to a first port 34 that is connected to an input 52 of a first pressure-to-movement conversion device 50 that is explained later.

As shown in FIG. 1B, when the patient is inhaling, the jet 9 of gas flowing across the inner chamber 5 is deflected and flows into the second receptor channel 36. The second receptor channel 36 is fluidly interfaced to a second port 38 which, in turn, is connected to an input 62 of a second pressure-to-movement conversion device 60 (see FIG. 2) which is explained later. In other embodiments, the jet 9 of gas is deflected or blocked by a device linked to a diaphragm, in particular for patients with very weak lung capacity.

Figure 4:
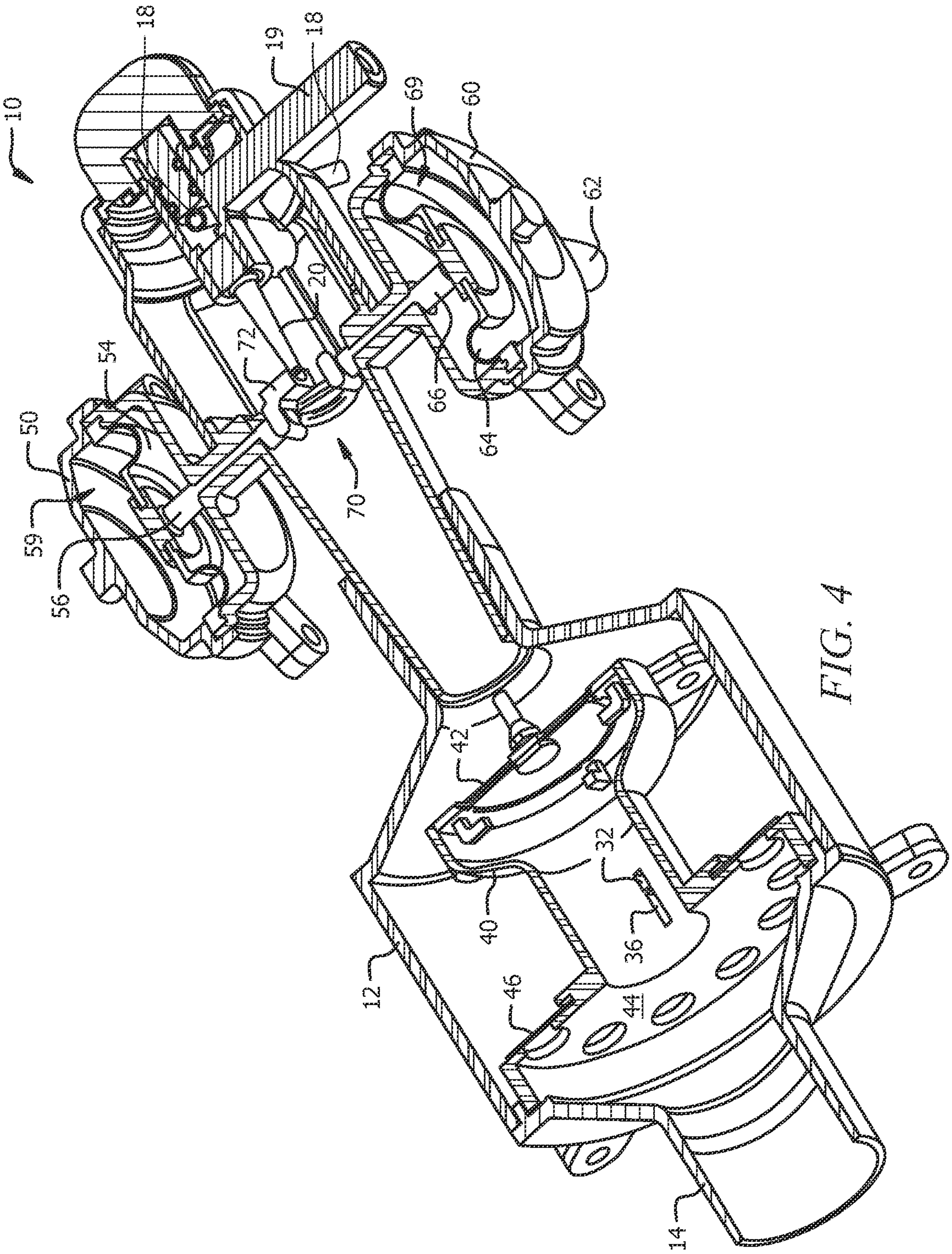
FIG. 4 illustrates another cut-away view of the mechanical bi-level positive airway pressure system.

The first pressure-to-movement conversion device 50 and the second pressure-to-movement conversion device 60 (see FIG. 2) push a movable occlusion device 70 that has an occluding member 72. The occluding member 72 is moved in front of the positive pressure nozzle 20 while the patient is not inhaling, thereby blocking gas pressure that continuously flows out of the positive pressure nozzle 20 until the patient starts to inhale. When the patient starts to inhale, the jet 9 of gas flowing across the inner chamber 5 is deflected and flows into the second receptor channel 36, which is in fluid communications with the second pressure-to-movement conversion device 60 that converts the gas pressure into a movement of the occluding member 72. The occluding member 72 moves to a position in which the gas pressure from the positive pressure nozzle 20 is no longer blocked. This provides positive pressure to the patient, helping the patient inhale. When the patient stops inhaling, the jet 9 of gas flowing across the inner chamber 5 relaxes and flows into the first receptor channel 32, which is in fluid communications with the first pressure-to-movement conversion device 50. The first pressure-to-movement conversion device 50 converts the gas pressure into a movement of the occluding member 72 to a position in which the gas pressure from the positive pressure nozzle 20 is blocked. This results in reducing the positive pressure and allowing for exhalation by the patient without needing to overcome the positive pressure. An example of pressure-to-movement conversion devices 50/60 and the movable occlusion device 70, including the occluding member 72 is shown in FIG. 4. It is fully anticipated that in some embodiments, a single pressure-to-movement conversion device operates on a pressure from one or the other of the first receptor channel 32 or the second receptor channel 36 using a resilient member or the resiliency of the diaphragm to return the occlusion device to the correct position after abatement of the gas pressure as in FIGS. 13A and 13B. Therefore, it is fully anticipated that in some embodiments, a single pressure-to-movement conversion device 50/60 is used and resilient force is used to return the occluding member 72 back to a resting position, examples of which are shown in FIGS. 11A, 11B, 12A, 12B, 13A and 13B. For example, a single pressure-to-movement conversion device 60 fluidly interfaced to the second receptor channel, in which the single pressure-to-movement conversion device 60 has a resilient diaphragm in which the resilient diaphragm works to pull the occluding member 72 into a resting position (see FIGS. 13A and 13B). When the patient inhales, the jet 9 of gas flowing across the inner chamber 5 bends and flows into the second receptor channel 36, thereby placing air pressure upon the resilient diaphragm, thereby overcoming the resilient force of the diaphragm and moving the occluding member 72 away from the positive pressure nozzle 20, providing positive pressure to the patient. When the patient stops inhaling, the jet 9 of gas flowing across the inner chamber 5 retorts to its natural flow and no longer enters the second receptor channel 36 and the resilient force of the diaphragm moves the occluding member 72 in front of the positive pressure nozzle 20, allowing the patient easier of exhalation.

A pressure relief valve 15 is provided to allow atmospheric air to flow out of the bi-level positive airway pressure system 10, allowing internal pressure to escape when a specific pressure is exceeded. Details of the pressure relief valve 15 are not shown for brevity and clarity reasons, though a typical pressure relief valve includes a spring-loaded ball valve, such that when pressure exceeds the force of the spring, the ball is pushed away from a seat, allowing pressure to escape.

In some embodiments, the intermediate channel 16 between the positive pressure nozzle 20 and the detection section 12 is tapered to a narrower diameter to increase the velocity of the gas as it moves toward the patient. In some embodiments, the taper is a linear taper as shown in the figures.

Figure 2:
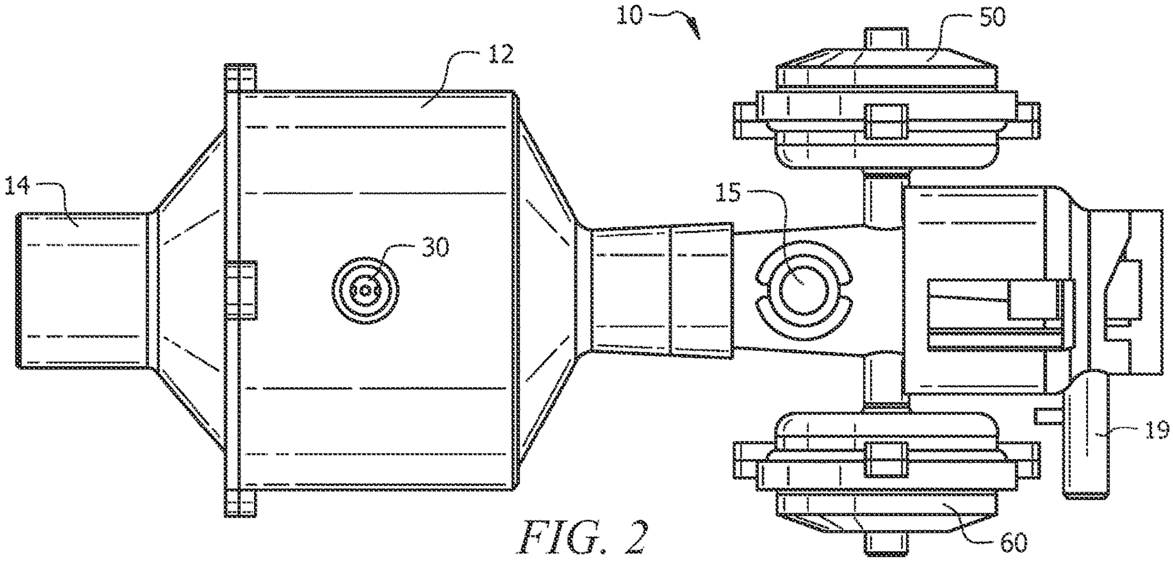
FIGS. 2 and 3 illustrate plan views of the mechanical bi-level positive airway pressure system.
Figure 3:
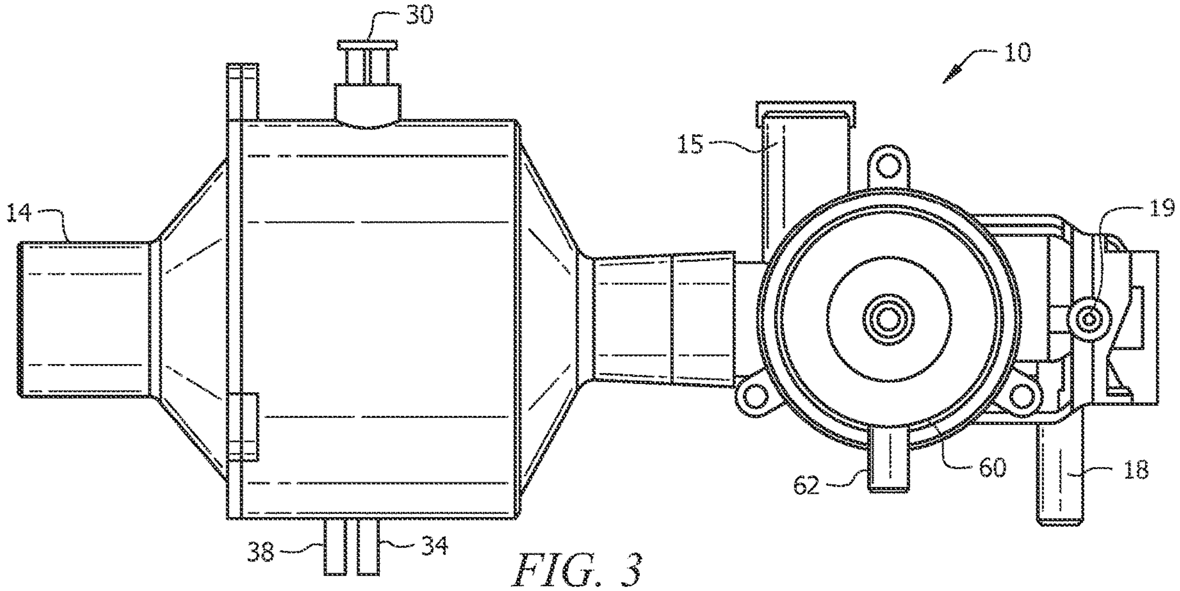

Referring to FIGS. 2 and 3, plan views of the mechanical bi-level positive airway pressure system 10 are shown. In this view, an exemplary outside enclosure including the detection section 12 is visible as well as both pressure-to-movement conversion devices. Gas, under pressure, is connected to the pressurized gas input 30 to create the jet 9 of gas. Gas, under pressure, is also connected to the positive pressure input port 18. Although it is anticipated that the same source of pressurized gas is provided to both the pressurized gas input 30 and the positive pressure input port 18, it is also anticipated that in other embodiments, different sources of gas are used, in some embodiments being the same gas under different pressures and in some embodiments being different gases.

Referring to FIG. 4, another cut-away view of the mechanical bi-level positive airway pressure system 10 is shown. In this view, construction of exemplary pressure-to-movement conversion devices 50/60 and the movable occlusion device 70, including the occluding member 72, is visible.

Each of the exemplary pressure-to-movement conversion devices 50/60 has a diaphragm 54/64 that is interfaced to a respective push rod 56/66. Air pressure from the respective ports 34/38 enter the pressure-to-movement conversion devices 50/60 from respective inputs 52/62 (see FIG. 5) that are in fluid communications with the outer chambers 59/69 surrounding the diaphragms 54/64. When air pressure enters the respective outer chamber 59/69, the air pressure pushes against the respective diaphragm 54/64, therefore, moving the respective push rods 56/66 in a direction towards the movable occlusion device 70. The push rods 56/66 are coupled to the movable occlusion device 70, thereby moving the occluding member 72 either in front of the positive pressure nozzle 20 (during exhalation) or away from the positive pressure nozzle 20 (during inhalation).

Note that the exemplary pressure-to-movement conversion devices 50/60 are examples and many other devices are anticipated that perform similar functions in various ways, including using pistons, etc. Again, it is noted that it is anticipated that in some embodiments, only a single pressure-to-movement conversion device 50/60 is present.

Figure 5:
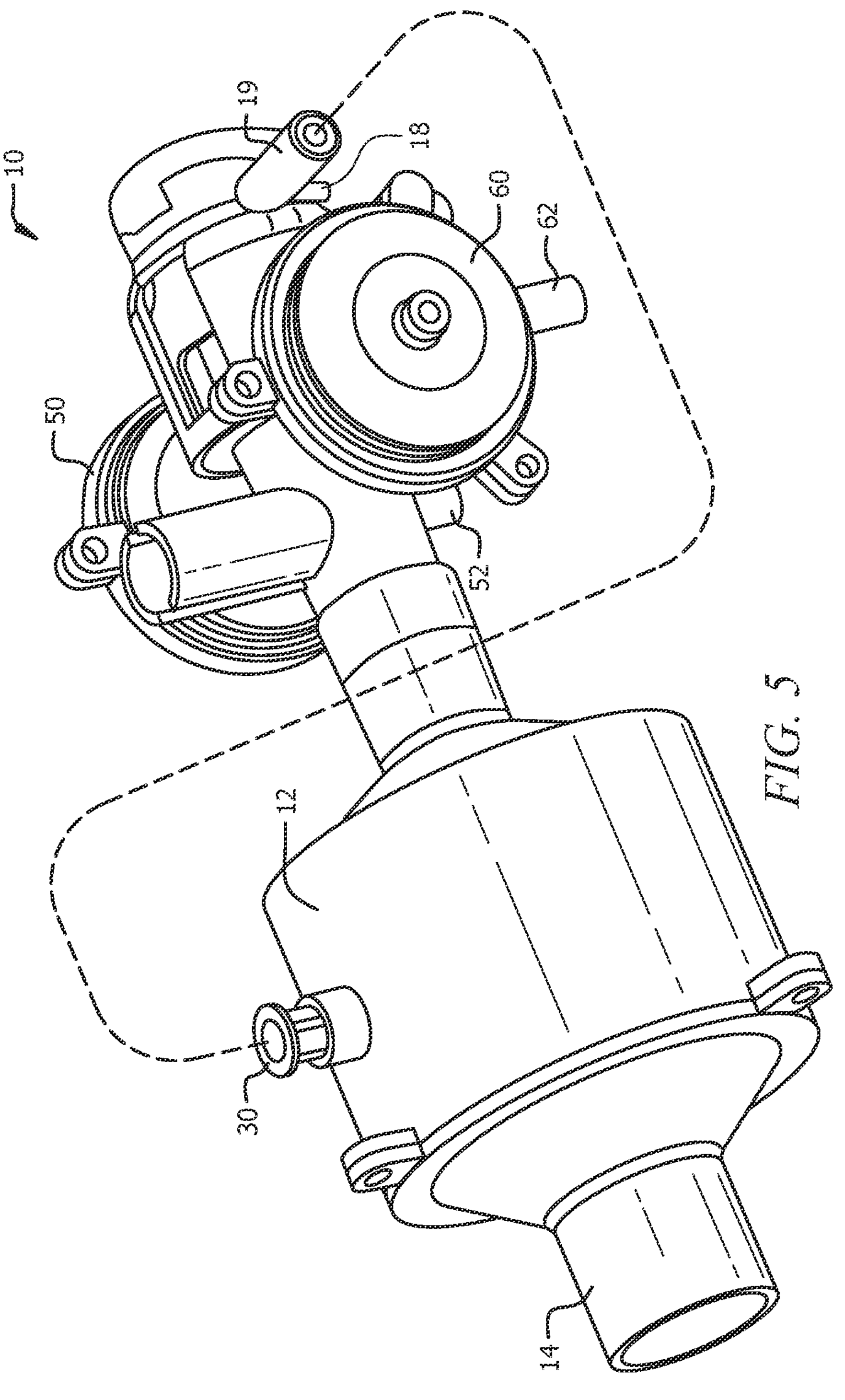
FIG. 5 illustrates a perspective view of the mechanical bi-level positive airway pressure system.

Referring to FIG. 5, a perspective view of the mechanical bi-level positive airway pressure system 10 is shown. It is anticipated that, for example, gas tubing connects both the pressurized gas input 30 and the positive pressure input port 18 to a source of pressurize gas (not shown for brevity reasons). It is also anticipated that the first port 34 is connected to the input 52 of a first pressure-to-movement conversion device 50 by a section of gas tubing (not shown for brevity reasons). Likewise, the second port 38 is connected to the input 62 of a second pressure-to-movement conversion device 60 by another section of gas tubing (not shown for brevity reasons). In alternate embodiments, it is equally anticipated that the first port 34 is directly connected to the input 52 of a first pressure-to-movement conversion device 50 through a channel formed in the body of the bi-level positive airway pressure system 10. Likewise, the second port 38 is directly connected to the input 62 of a second pressure-to-movement conversion device 60 through another channel formed in the body of the bi-level positive airway pressure system 10.

Figure 6A:
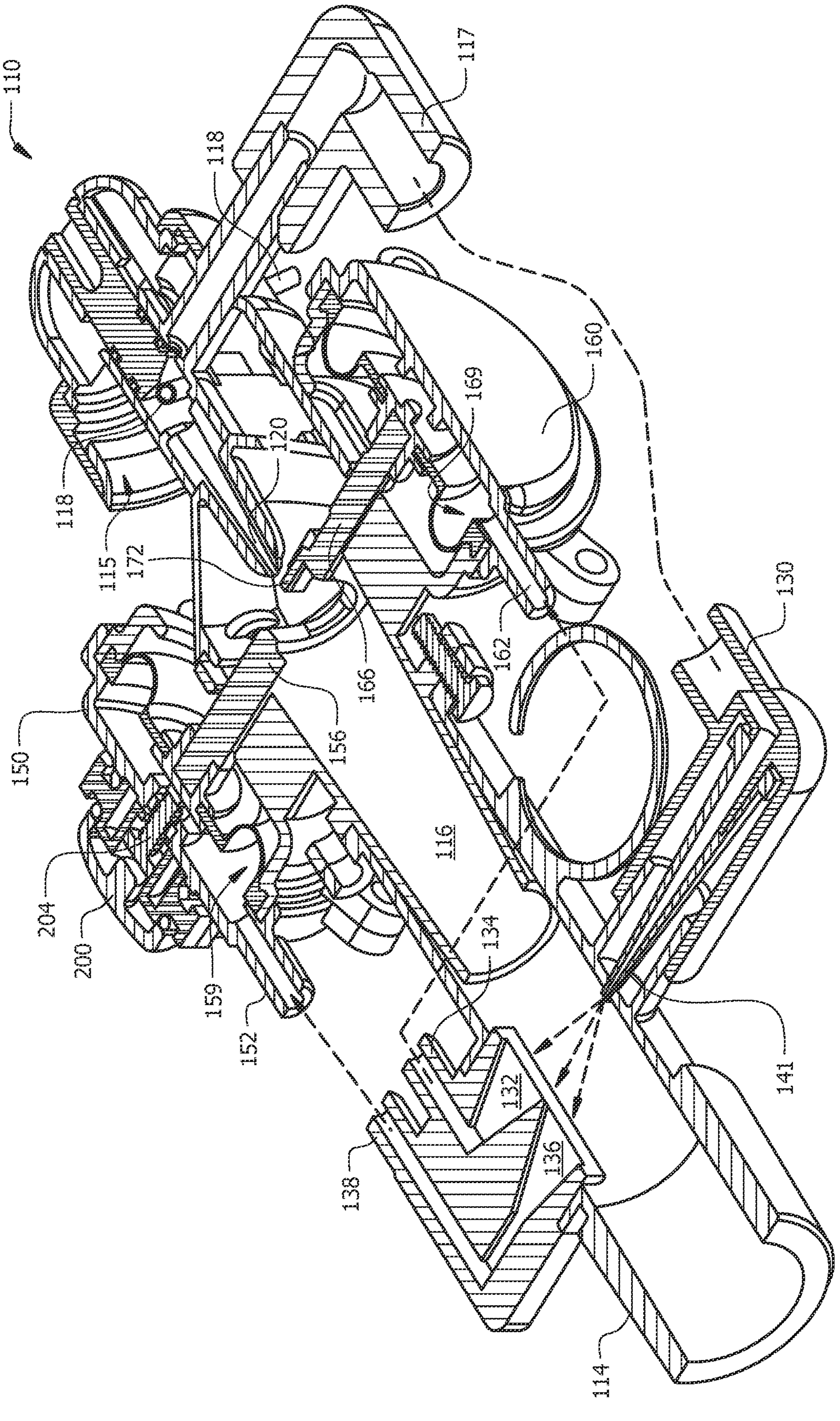
FIGS. 6A, 6B and 6C illustrate cut-away perspective views of a second mechanical bi-level positive airway pressure system.
Figure 6B:
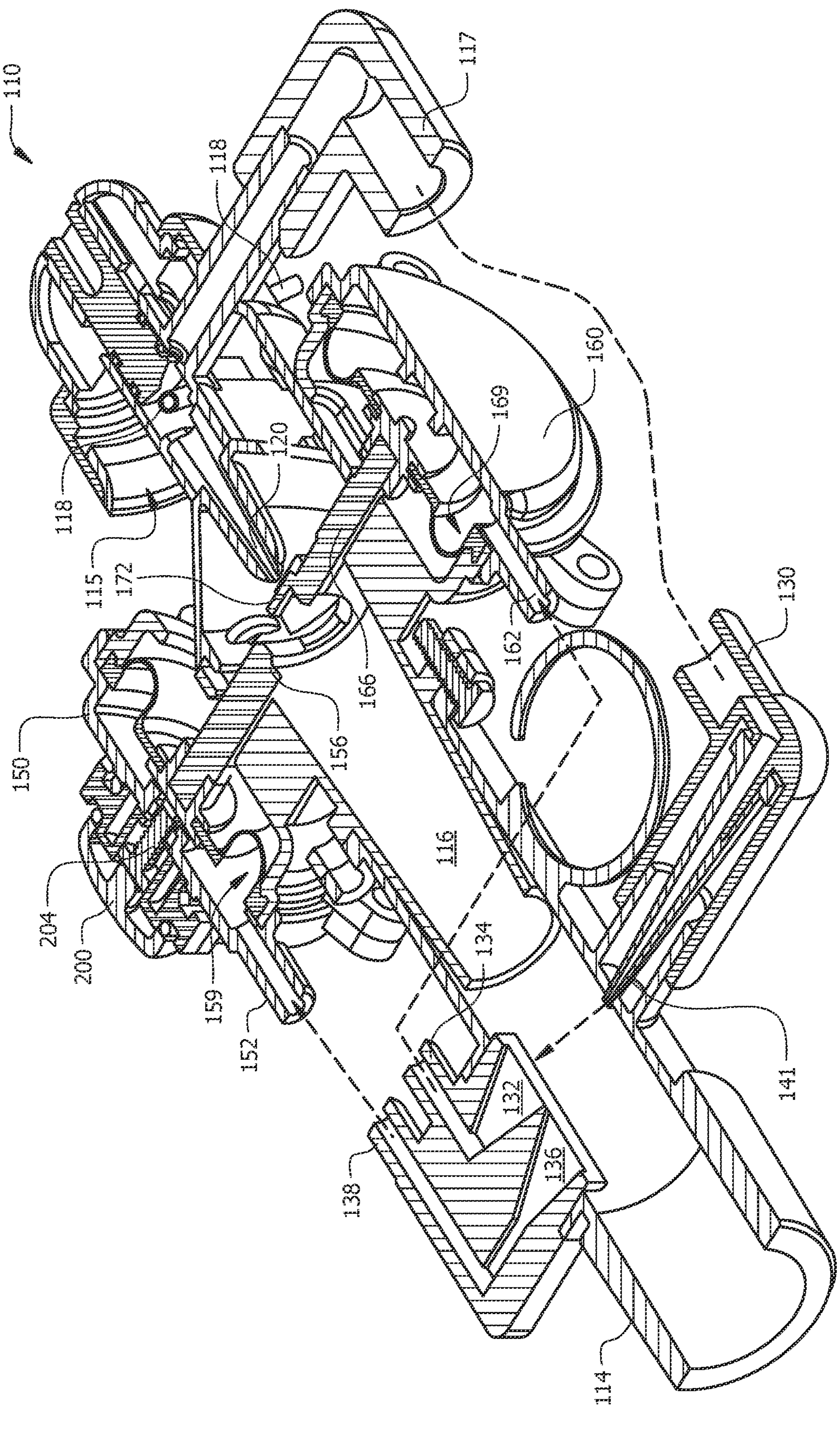
Figure 6C:
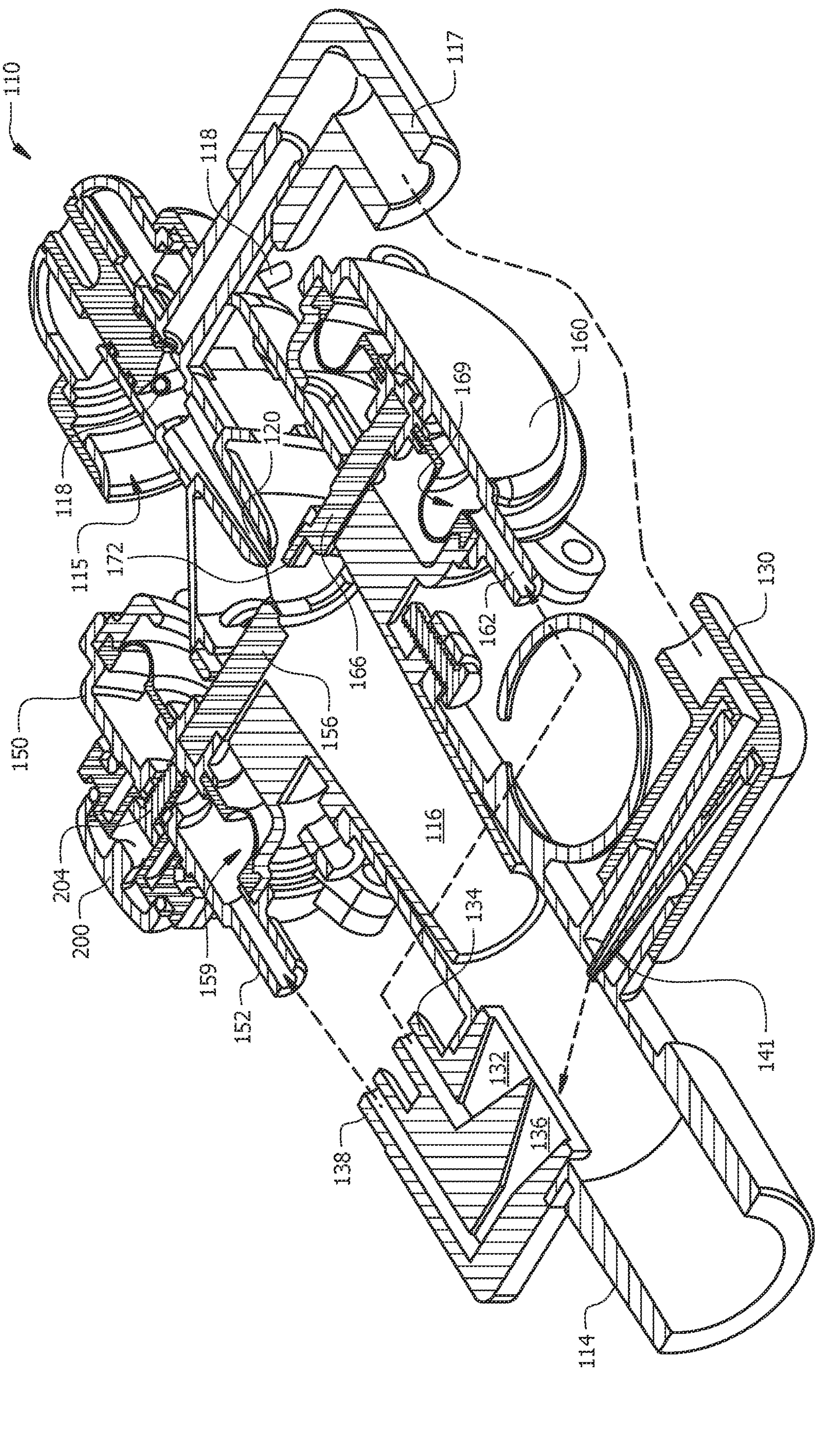

FIGS. 6A, 6B and 6C illustrate cut-away perspective views of a second mechanical bi-level positive airway pressure system 110. The second mechanical bi-level positive airway pressure system 110 functions similar to the mechanical bi-level positive airway pressure system 10 described previously without the need for one-way valves.

In FIGS. 6A, 6B and 6C, the patient airway (not shown) is interfaced to the patient port 114 by any way known in the industry such as by a nasal cannula, facemask, endotracheal tube, etc.

The intent of any bi-level positive airway pressure system is to provide assisted inhalation to a patient during inhalation while reducing this assistance during exhalation to make it easier to exhale.

The mechanical bi-level positive airway pressure system 110 as shown in FIGS. 6A, 6B and 6C accomplish such through a feedback system that provides positive air pressure until the patient exhales, at which time the source of the positive air pressure is blocked, thereby allowing the patient to exhale.

The components of the second mechanical bi-level positive airway pressure system 110 are shown in FIG. 6A. The breath detection sub-system includes a nozzle 141 that is in fluid communications with a source of air pressure connected to a port 130. As shown in FIG. 6A, a jet of gas crosses the path of the breath to/from the patient port 114. At rest, the jet of gas flows directly across the patient port 114 and enters both receptor channels 132/136 as depicted by the center arrow (e.g., equally or approximately equally). In some embodiments, the jet of gas is biased toward the forward receptor channel 136. In some embodiments, the jet of gas is biased toward the rear receptor channel 132. In other embodiments, the jet of gas is not biased towards either the forward receptor channel 136 or the rear receptor channel 132.

As the patient inhales, the jet of air bends more toward the forward receptor channel 136. As the patent exhales, the jet of air bends more toward the rear receptor channel 132.

The forward receptor channel 136 has a first connector 138 that is in fluid communications with a first diaphragm 159 through a first diaphragm port 152. For example, a tube 137 (see FIG. 7) or hose that connects the first connector 138 with the first diaphragm port 152.

The rear receptor channel 132 has a second connector 134 that is in fluid communications with a second diaphragm 169 through a second diaphragm port 162. For example, a second tube 135 or hose connects the second connector 134 with the second diaphragm port 162.

The first diaphragm 159 is in a first housing 150 and the second diaphragm 169 is in a second housing 160. The first diaphragm 159, when supplied with gas pressure, pushes on a first displacement rod 156 and the second diaphragm 169, when supplied with gas pressure, pushes in an opposite direction on a second displacement rod 166. The first displacement rod 156 is interfaced to the second displacement rod 166 creating a push-push system where the first diaphragm 159 pushes the displacement rods 156/166 in one direction and the second diaphragm 169 pushes the displacement rods 156/166 in the opposite direction. The displacement rods 156/166 move an occluding member 172 accordingly, either away from the source of airway pressure 120 during inhalation or in front of and blocking the source of airway pressure 120 during exhalation.

In some embodiments, a bias adjustment mechanism 200 is provided. The bias adjustment mechanism 200 adjusts an offset of the occluding member 172 through, for example, a screw mechanism. By turning the bias adjustment mechanism 200 in one direction, the occluding member 172 is moved slightly out of occlusion of the source of airway pressure 120 and by turning the bias adjustment mechanism 200 in the opposite direction, the occluding member 172 is moved slightly further into occlusion of the source of airway pressure 120.

In some embodiments, the intermediate channel 116 between the source of airway pressure 120 and the patient port 114 is tapered (e.g., frustum-shaped) to a narrower diameter to increase the velocity of the gas as it moves toward the patient. In some embodiments, the taper is a linear taper as shown in the figures. The taper of the intermediate channel 116 accelerates the flow of air and provide greater positive airway pressure utilizing less pressurized gas from a source of gas connected to the gas source port 118.

Note that it is anticipate, though not required, that both the gas source port 118 and the port 130 be connected to the same source of pressurized gas, such as an oxygen tank, hospital oxygen port, etc.

Note that in some embodiments, a coupling port 117 is provided to interface the gas source port 118 and provide gas pressure to the port 130 through, for example, a tube connecting the coupling port 117 and the port 130.

Figure 13A:
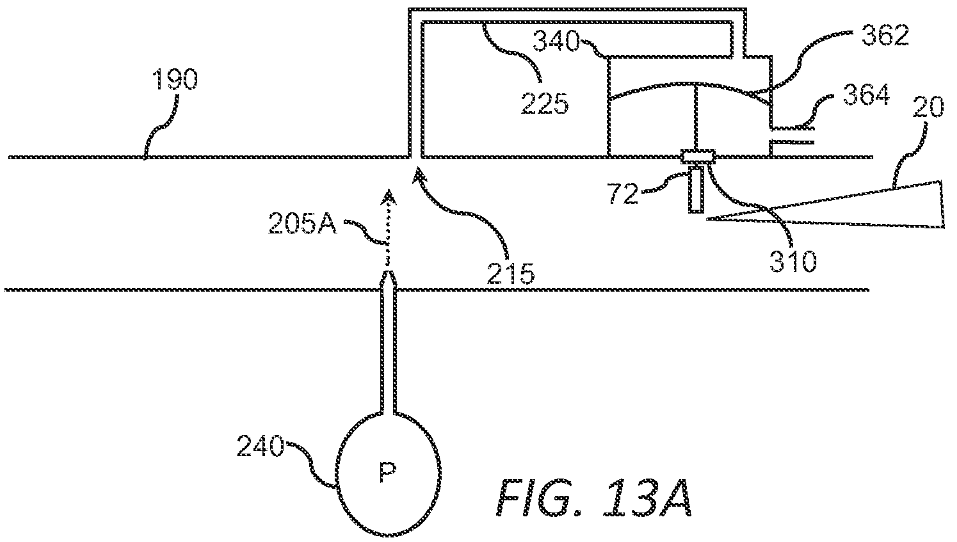
FIGS. 13A and 13B illustrate schematic views of a device for detecting a flow using a single, resilient diaphragm within a chamber.
Figure 13B:
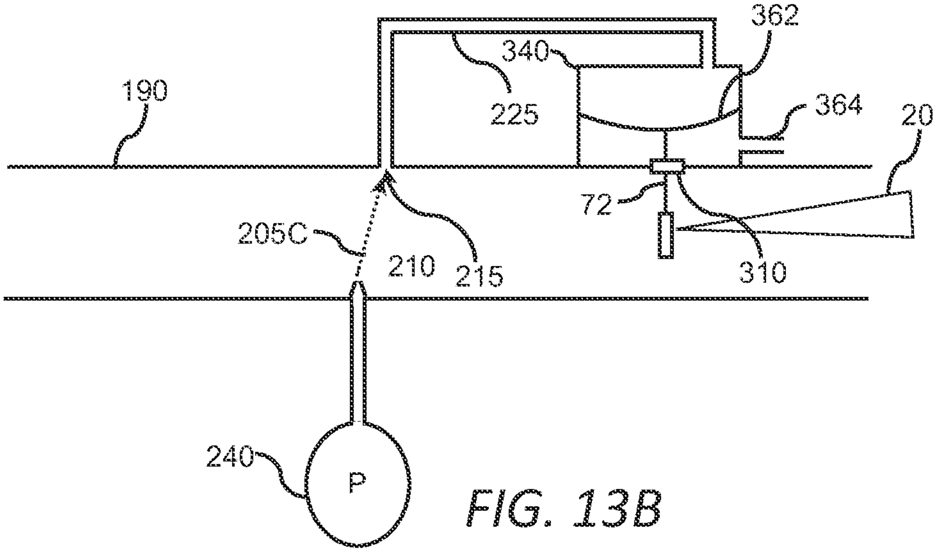

Note also that, in some embodiments, a single, first diaphragm 159 coupled to a single forward receptor channel 136 (see example in FIGS. 13A and 13B). In this, the resiliency of the single, first diaphragm 159 returns the occluding member 172 to occlude the source of airway pressure 120 when the exhalation occurs.

Starting from the position shown in FIG. 6A, when exhalation occurs as shown by exhalation arrows in FIG. 6B, the flow of air from the patient flows into the mechanical bi-level positive airway pressure system 110 from the patient port 114 as indicated by the jet flow arrow in FIG. 6B. The flow of air from the patient deflects the jet of air from the nozzle 141 such that the jet of air is received by the rear receptor channel 132. The rear receptor channel 132 is in fluid communication with the second diaphragm 169 that pushes the second displacement rod 166, moving the occluding member 172 to a position where it blocks the source of airway pressure 120. The result is that the occluding member 172 abates or reduces the positive airway pressure provided to the patient port 114, making it easier for exhalation.

Now, referring to FIG. 6C, when inhalation occurs, the flow of air from the mechanical bi-level positive airway pressure system 110 towards the patient port 114 as indicated by the air flow arrow in FIG. 6C. The flow of air towards the patient port 114 deflects the jet of air from the nozzle 141 such that the jet of air is now received by the forward receptor channel 136. The forward receptor channel 136 is in fluid communication with the first diaphragm 159 that pushes the first displacement rod 156. This moves the occluding member 172 to a position where it does not block the source of airway pressure 120, thereby providing the positive airway pressure to the patient port 114, making it easier for inhalation.

Exhaust port(s) 115 (see FIG. 8) are provided to allow atmospheric air to flow in/out of the bi-level positive airway pressure system 110, allowing the exhalation gases to escape and allowing fresh air to enter during inhalation.

Figure 7:
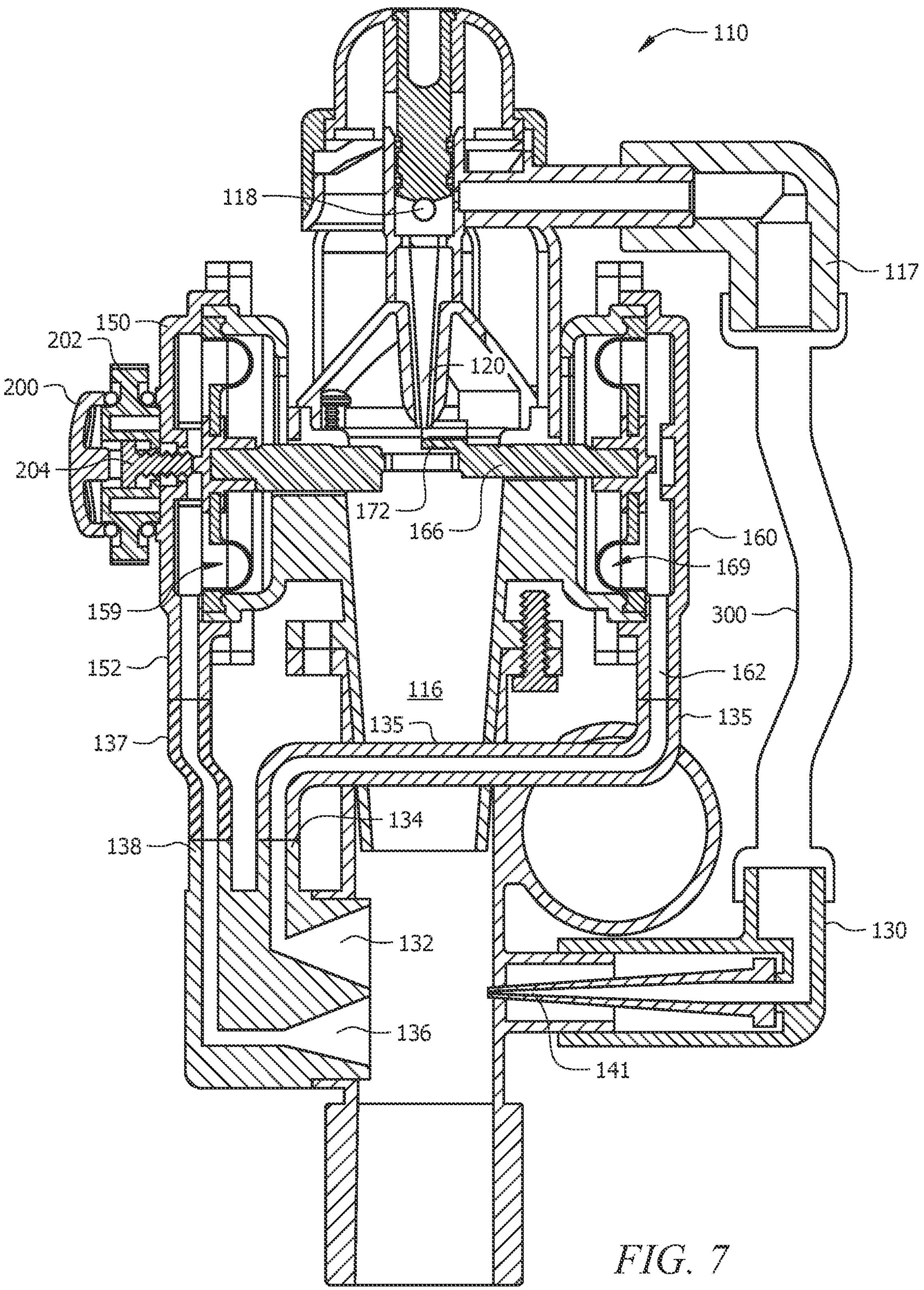
FIG. 7 illustrates a cut-away plan view of the second mechanical bi-level positive airway pressure system.

FIG. 7 illustrates a cut-away plan view of the second mechanical bi-level positive airway pressure system 110. In this view, the bias adjustment mechanism 200 is shown connected to a torquing component 202 that connects to a biasing screw 204. Note that the bias adjustment mechanism 200/202/204 is optional.

Figure 8:
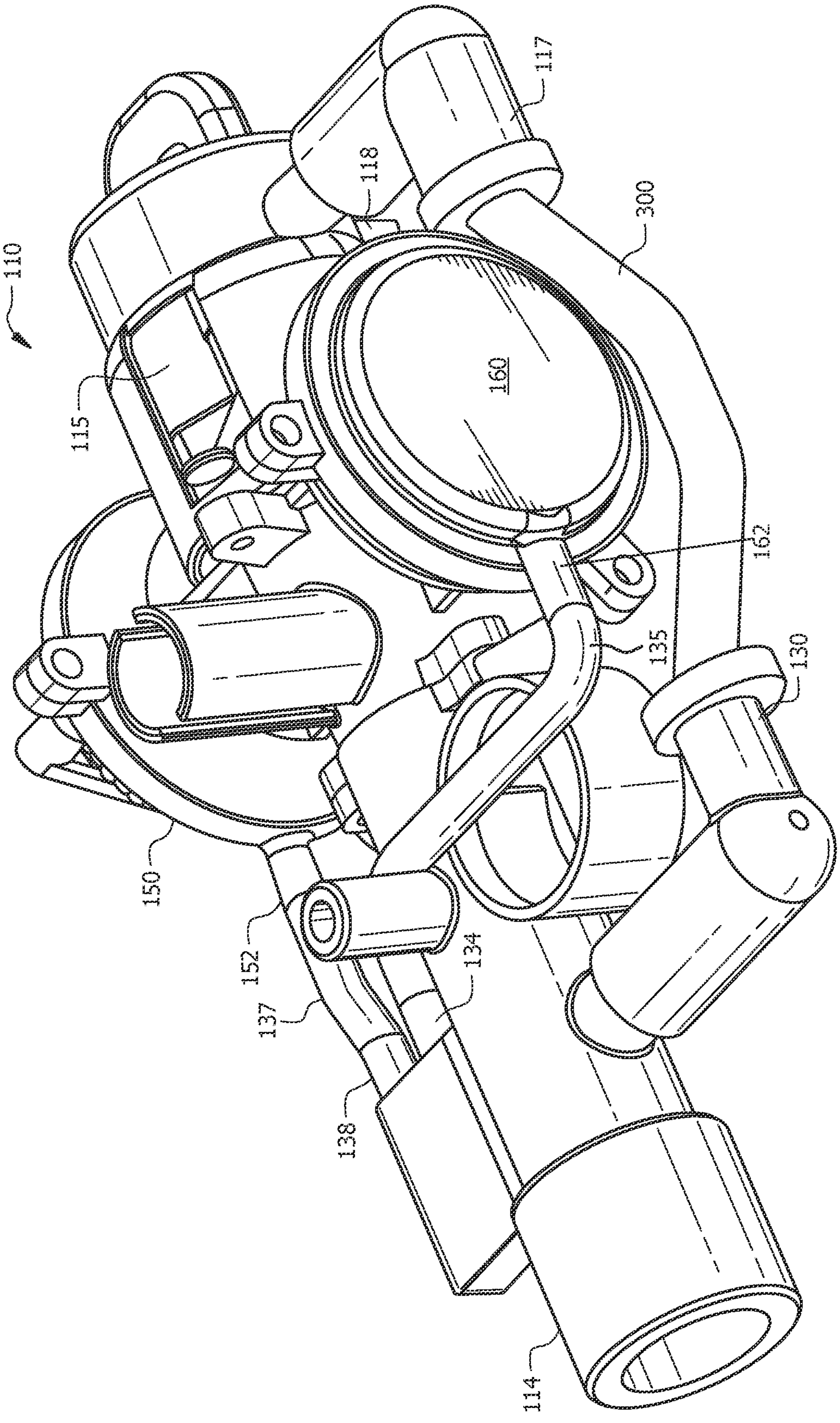
FIG. 8 illustrates a perspective view of the second mechanical bi-level positive airway pressure system.

FIG. 8 illustrates a perspective view of a physical embodiment of the second mechanical bi-level positive airway pressure system 110. As discussed, in this physical embodiment of the mechanical bi-level positive airway pressure system 110, a tube 137 connects a first connector 138 with the first diaphragm port 152 and a second tube 135 connects the second connector 134 with the second diaphragm port 162. It is also fully anticipated to interconnect such with any known mechanism including channels embedded within the housing of the mechanical bi-level positive airway pressure system 110.

Figure 9A:
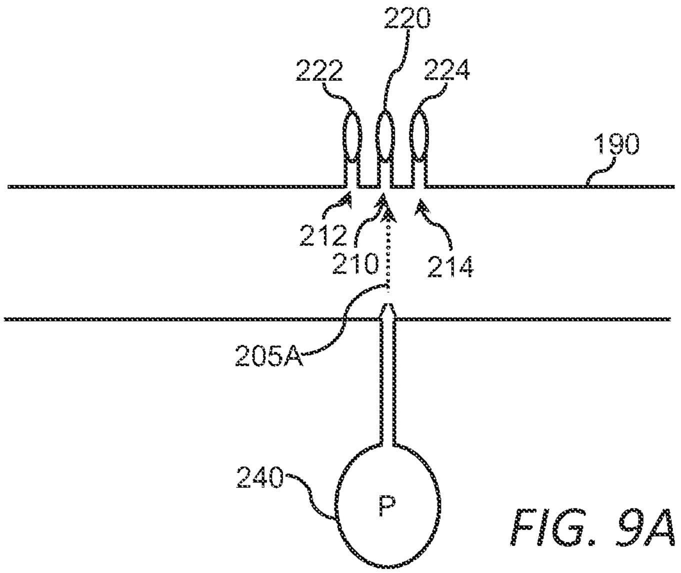
FIGS. 9A, 9B, and 9C illustrate schematic views of a device for detecting a flow of a gas.
Figure 9B:
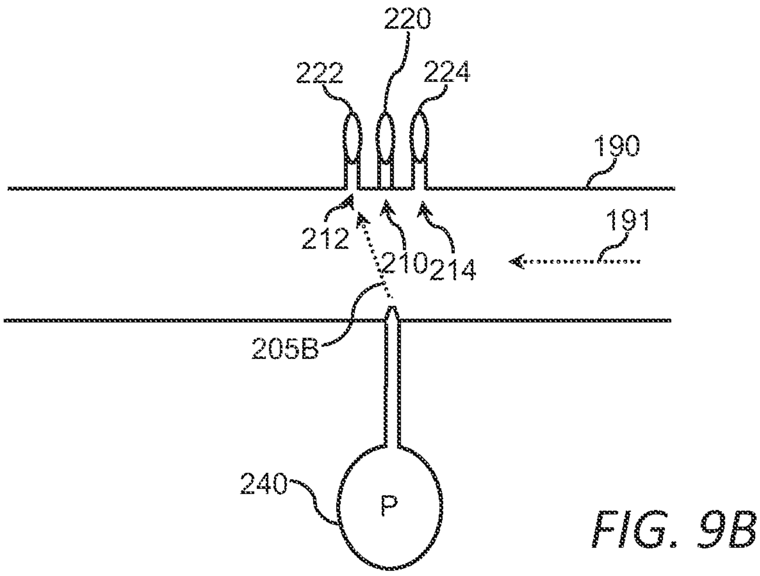
Figure 9C:
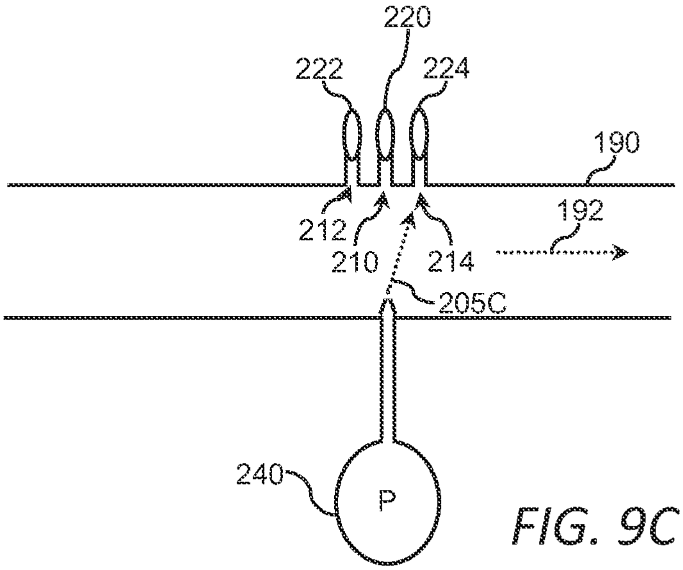

Referring to FIGS. 9A, 9B, and 9C, schematic views of a device for detecting a flow of a gas are shown. The device for detecting a flow of a gas emits a jet of gas 205A from a source of pressurized gas 240 (e.g., air pressure). The jet of gas 205A is directed across the conduit 190 in which the flow of gas is expected and needs to be detected. As shown in FIG. 9A, the jet of gas 205A travels across the conduit 190 and enters a main port 210 that is connected to a first sensor 220 (e.g., a pressure sensor). Until a flow of gas within the conduit 190 occurs, the jet of gas 205A flows directly across the conduit 190 and into the main port 210. Therefore, a reading or signal at the first sensor 220 of a higher pressure caused by the jet of gas 205A indicates that there is no flow of gas within the conduit 190.

When a flow of gas occurs within the conduit 190 (down-stream flow), the jet of gas 205A is deflected. In FIG. 9B, the flow of gas within the conduit 190 is in a first direction (e.g., down-stream flow) or a right-to-left flow 191, deflecting the jet of gas 205B into a down-stream port 212 that is connected to a second sensor 222. Therefore, a reading of a higher pressure from the second sensor 222 indicates that there is right-to-left flow 191 of gas within the conduit 190.

Likewise, in FIG. 9C, the flow of gas within the conduit is a second direction (up-stream) or left-to-right flow 192, deflecting the jet of gas 205C into an up-stream port 214 that is connected to a third sensor 224. Therefore, a reading of a higher pressure from the third sensor 224 indicates that there is left-to-right flow 192 of gas within the conduit 190.

In this example, three ports (down-stream port 212, main port 210, and up-stream port 214) with three sensors (second sensor 222, first sensor 220, and third sensor 224) are used to indicate right-to-left flow 191, no flow, and left-to-right flow 192, respectively. It is fully anticipated that, in some embodiments, less ports and sensors are provided depending upon what information is needed. For example, if it is only needed to determine if there is a flow, without need to know a direction, only one port and sensor is needed, for example, only the main port 210 and the first sensor 220. Reception of a signal indicating a higher pressure from the first sensor 220 indicates no flow and a signal of a lower pressure from the first sensor 220 indicates flow in either direction. Likewise, in another embodiment, flow and direction detection is determined having a down-stream port 212, a second sensor 222, an up-stream port 214, and a third sensor 224. A signal of a higher pressure at the second sensor 222 indicates right-to-left flow 191, a signal of a higher pressure from the third sensor 224 indicates left-to-right flow 192, and a signal of a lower pressure from both the second sensor 222 and the third sensor 224 indicate lack of flow of gas within the conduit 190.

Figure 10:
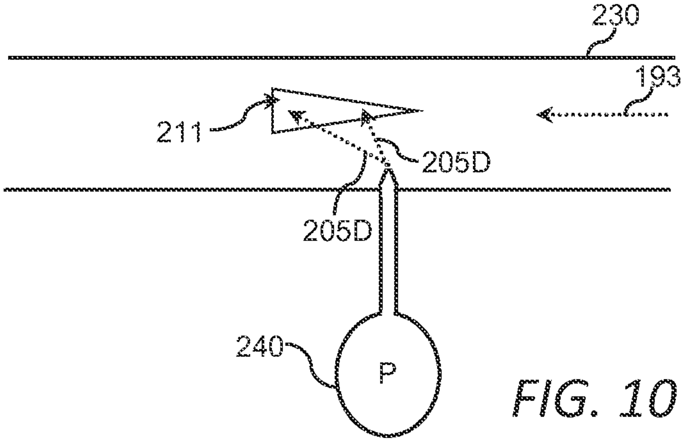
FIG. 10 illustrates a schematic view of a device for detecting a velocity of flow of a gas.

Referring to FIG. 10, a schematic view of a device for detecting a velocity of flow of a gas is shown. In this example, a conduit 230 is equipped with a graduated port 211 (shown triangular, though any shape of the graduated port 211 is anticipated). In this example, a variable right-to-left flow 193 is shown. When there is no flow of gas in the conduit 230, the gas jet crosses the conduit 230 (not shown) and either misses the graduated port 211 or enters the graduated port 211 at an apex. When the rate of right-to-left flow 193 of gas in the conduit 230 is low, the gas jet 205D crosses the conduit and enters at a smaller opening of the graduated port 211. When the rate of right-to-left flow 193 of gas in the conduit 230 is higher, the gas jet 205D crosses the conduit and enters at a larger opening of the graduated port 211.

In such, when there is no right-to-left flow 193 of gas in the conduit 230, a pressure sensor interfaced to the graduated port 211 reads a low pressure. When there is a low rate of right-to-left flow 193 of gas in the conduit 230, the pressure sensor interfaced to the graduated port 211 reads a higher pressure. When there is a higher rate of right-to-left flow 193 of gas in the conduit 230, the pressure sensor interfaced to the graduated port 211 reads an even higher pressure. In this way, the pressure measured by the sensor interfaced to the graduated port 211 is an indication of the rate (velocity) of right-to-left flow 193 of gas in the conduit 230. In some embodiments, instead of the graduated port 211, multiple discrete ports are provided, for example, sized orifices. In some embodiments, there are two graduated ports 211 for detecting bi-directional rates of flow of gas in the conduit 230 or one graduated port 211 and one or more down-stream port 212, main port 210, and/or up-stream port 214. This provides, for example, flow rate values in both directions or flow rate values for one direction of flow with an indication of flow in the opposing direction. Further, in some embodiments, the taper of the graduated port(s) 211 is reversed.

Note that it is fully anticipated that the pressure sensors (e.g., first pressure sensor 220, second pressure sensor 222, third pressure sensor 224) are any electrical, pneumatic, and/or mechanical sensors that detect pressures, either in a digital fashion (e.g., absence or presence of pressure) or in an analog fashion (e.g., detect a pressure gradient). Examples of such are electronic pressure sensors, diaphragm operated devices, etc. It is also fully anticipated that the pressure sensors be interfaced/connected to any mechanical/electrical/pneumatic device for any purpose. Examples of such are devices to indicate air flow and/or direction, devices to control/redirect air flow, alarms, etc.

Figure 11A:
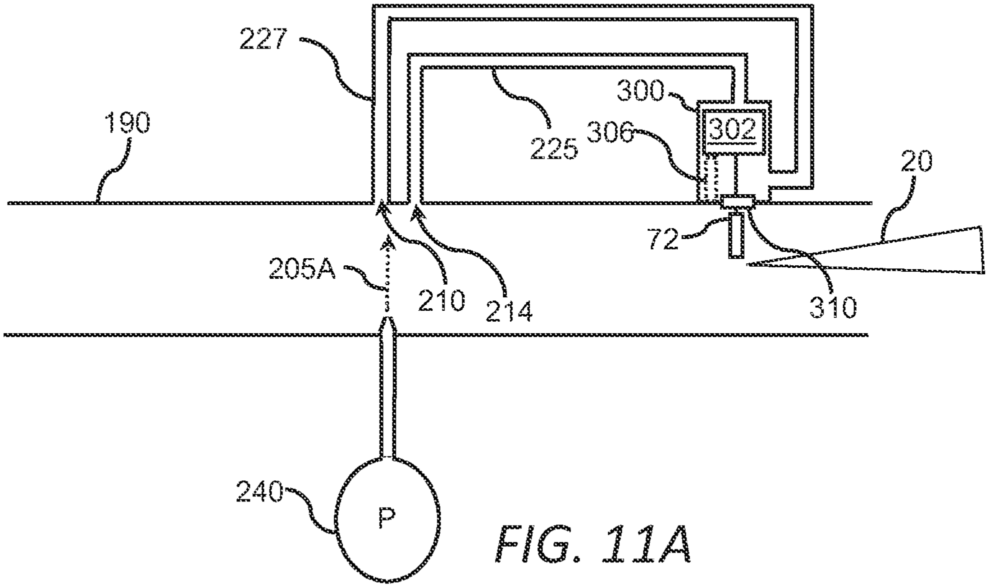
FIGS. 11A and 11B illustrate schematic views of a device for detecting a flow using a gas using a piston within a cylinder.
Figure 11B:
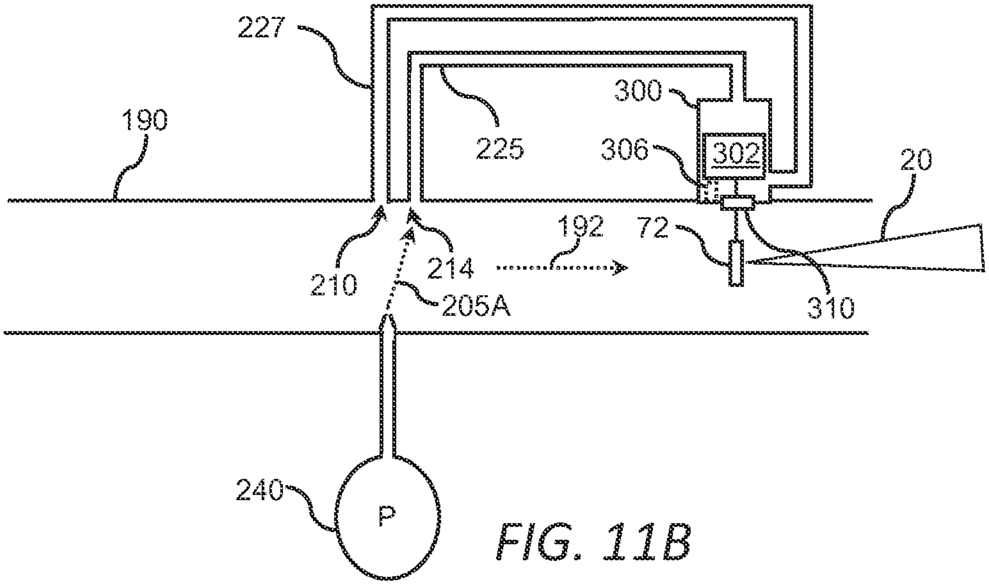

Referring to FIGS. 11A and 11B, schematic views of a device for detecting a flow of a gas using a piston 302 within a cylinder 300 are shown. The device for detecting a flow of a gas emits a jet of gas 205A from a source of pressurized gas 240 (e.g., air pressure). The jet of gas 205A is directed across the conduit 190 in which the flow of gas is expected and needs to be detected (e.g., exhalation). As shown in FIG. 11A, in absence of exhalation, the jet of gas 205A travels across the conduit 190 and enters a first port 210 that is connected to lower input of a cylinder 300 (e.g., the pressure sensor). This gas pressure forces a piston 302 toward the top end of the cylinder 300 (away from the positive pressure nozzle 20), thereby retracting the occluding member 72 and providing positive airway pressure. When a flow of gas occurs within the conduit 190 (e.g., during exhalation) as in FIG. 11B, the jet of gas 205A deflects and flows angularly across the conduit 190 and into the second port 214. Gas entering the second port 214 pressurizes the top area of the cylinder 300 and, as pressure is no longer entering the first port 210, the pressure at the top of the cylinder 300 pushes the piston 302 downwardly and towards the positive pressure nozzle 20 and the occluding member 72 is moved in position to block the positive pressure nozzle 20, thereby reducing positive airway pressure while the patient is exhaling. In some embodiments, a weak spring 306 provides biasing of the piston 302 and, hence, the occluding member 72 towards the non-blocking mode. Also, being that air pressure exists within the conduit 190, in some preferred embodiments, a very low leakage and very low friction seal 310 seals the cylinder from the conduit 190.

In this example, only one device (cylinder 300 and piston 302) is required to facilitate movement of the occluding member 72 to selectively block the positive airway pressure 20. Note that this mechanism requires a very easily, light-weight piston 302 and a very low loss, low friction seal 310 and/or a higher pressure source of pressurized gas 240.

Note that tubes 227/225 connect the first port 210 and second port 214 to the cylinder 300.

Figure 12A:
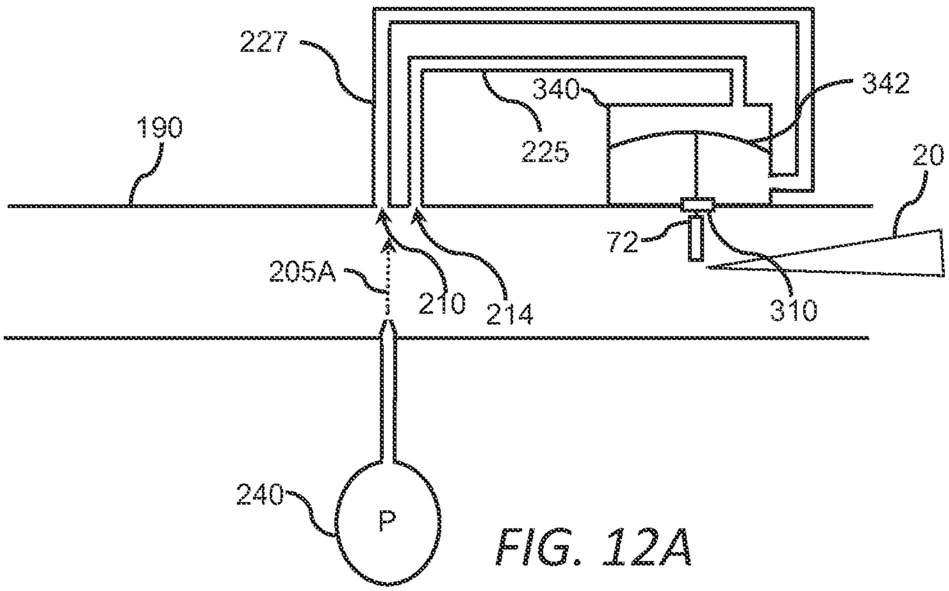
FIGS. 12A and 12B illustrate schematic views of a device for detecting a flow using a single diaphragm.
Figure 12B:
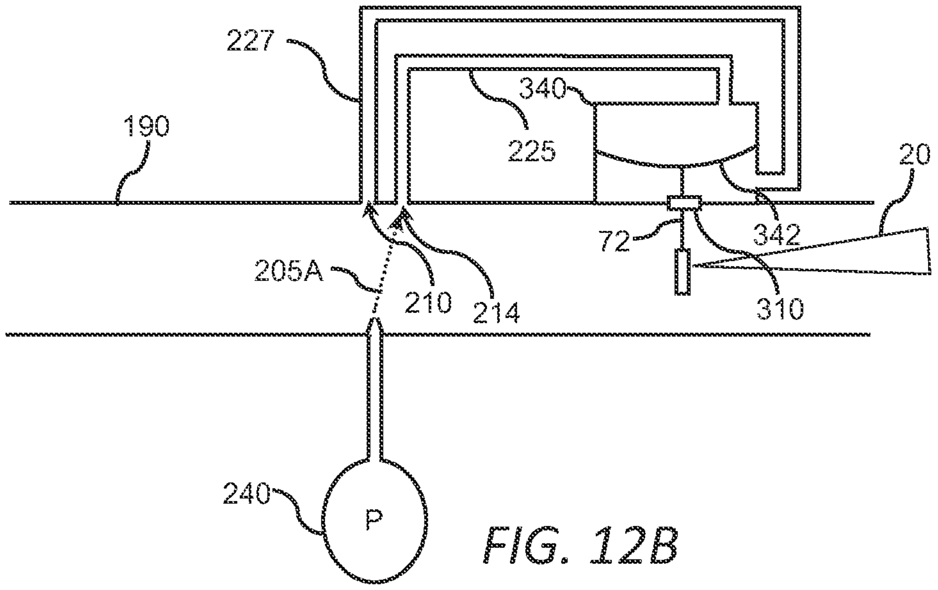

Referring to FIGS. 12A and 12B, schematic views of a device for detecting a flow using a single diaphragm 342 mounted within a chamber 340 are shown. The device for detecting a flow of a gas emits a jet of gas 205A from a source of pressurized gas 240 (e.g., air pressure). The jet of gas 205A is directed across the conduit 190 in which the flow of gas is expected and needs to be detected (e.g., exhalation). As shown in FIG. 12A, in absence of exhalation, the jet of gas 205A travels across the conduit 190 and enters a first port 210 that is connected to lower input of a chamber 340 (e.g., the pressure sensor) on a first side of the diaphragm 342. This gas pressure forces a diaphragm 342 to bow upward within the chamber 340 (away from the positive pressure nozzle 20), and, as the occluding member 72 is connected to the diaphragm 342, the occluding member 72 is retracted, thereby providing positive airway pressure. When a flow of gas occurs within the conduit 190 (e.g., during exhalation) as in FIG. 12B, the jet of gas 205A deflects and flows angularly across the conduit 190 and into the second port 214. Gas entering the second port 214 pressurizes the top area of the chamber 340 and, as pressure is no longer entering the first port 210, the pressure at the top of the chamber 340 pushes the diaphragm 342 downwardly and towards the positive pressure nozzle 20 and the occluding member 72 is moved in position to block the positive pressure nozzle 20, thereby reducing positive airway pressure while the patient is exhaling. Being that air pressure exists within the conduit 190, in some preferred embodiments, a very low leakage and very low friction seal 310 seals the chamber 340 from the conduit 190.

In this example, only one device (Chamber 340 and diaphragm 342) is required to facilitate movement of the occluding member 72 to selectively block the positive airway pressure 20. Note that this mechanism requires a very low loss, low friction seal 310 and/or a higher pressure source of pressurized gas 240.

Note that tubes 227/225 connect the first port 210 and second port 214 to the chamber 340.

Referring to FIGS. 13A and 13B, schematic views of a device for detecting a flow using a single, resilient diaphragm 362 within a chamber 360 are shown. The device for detecting a flow of a gas emits a jet of gas 205A from a source of pressurized gas 240 (e.g., air pressure). The jet of gas 205A is directed across the conduit 190 in which the flow of gas is expected and needs to be detected (e.g., exhalation). As shown in FIG. 13A, in absence of exhalation, the jet of gas 205A travels across the conduit 190 and does not enter the port 215. Therefore, the resilient diaphragm 362 remains within its natural position, deflected upward, away from the positive pressure nozzle 20. In such, the occluding member 72 is connected to the resilient diaphragm 362 and the occluding member 72 is retracted, thereby providing positive airway pressure. When a flow of gas occurs within the conduit 190 (e.g., during exhalation) as in FIG. 13B, the jet of gas 205A deflects and flows angularly across the conduit 190 and into the port 215. Gas entering the port 215 pressurizes the top area of the chamber 360 and overcomes the resiliency of the resilient diaphragm 362, pushing the resilient diaphragm 362 downwardly and towards the positive pressure nozzle 20 and the occluding member 72 is moved in position to block the positive pressure nozzle 20, thereby reducing positive airway pressure while the patient is exhaling. Being that air pressure exists within the conduit 190, in some preferred embodiments, a very low leakage and very low friction seal 310 seals the chamber 340 from the conduit 190.

In this example, only one device (chamber 360 and resilient diaphragm 362) is required to facilitate movement of the occluding member 72 to selectively block the positive airway pressure 20. Note that this mechanism requires a very low loss, low friction seal 310 and/or a higher pressure source of pressurized gas 240.

Equivalent elements can be substituted for the ones set forth above such that they perform in substantially the same manner in substantially the same way for achieving substantially the same result.

In a preferred embodiment, the chamber 360 is vented by a vent 364 to atmospheric pressure. Note that tube 225 connect the port 211 to the chamber 360.

It is believed that the system and method as described and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A bi-level positive airway pressure device comprising:

a housing having a patient port for connecting to an airway of a patient;

means for generating a positive airway pressure directed through a conduit towards the patient port; and an exhalation detector comprising a nozzle emitting a jet of a gas directed across the conduit, the jet of the gas is directed at a receptor channel when exhalation gases flow from the patient port, thereby an increase a gas pressure is present at the receptor channel when the exhalation gases flow from the patient port, and the exhalation detector having means to convert the increase in the gas pressure into a movement of an occluding member such that when the exhalation gases flow from the patient port, the occluding member moves to block the means for generating the positive airway pressure.

2. The bi-level positive airway pressure device of claim 1, wherein the means to convert the increase in the gas pressure comprises a resilient diaphragm that seals a chamber into two sections, the resilient diaphragm mechanically interfaced to the occluding member and the resilient diaphragm is biased towards a first section of the two sections; the first section is fluidly interfaced to the receptor channel such that when the exhalation gases flow from the patient port, the increase in the gas pressure exerts force on the resilient diaphragm to deform the resilient diaphragm and move the occluding member to block the means for generating the positive airway pressure.

3. The bi-level positive airway pressure device of claim 1, further comprising a second receptor channel positioned such that the jet of the gas is directed at the second receptor channel when the exhalation gases abate from the patient port, thereby the increase in the gas pressure is present in the second receptor channel.

4. The bi-level positive airway pressure device of claim 3, wherein the means to convert the increase in the gas pressure comprises a piston in a cylinder, the piston is mechanically interfaced to the occluding member; a first side of the cylinder is fluidly interfaced to the receptor channel and a second side of the cylinder is fluidly interfaced to the second receptor channel such that when the exhalation gases flow from the patient port, the increase in the gas pressure at the first side of the piston exerts a force on the first side of the piston to move the piston, and therefore, the occluding member to block the means for generating the positive airway pressure and when the exhalation gases abate, the increase in the gas pressure in the second side of the piston exerts an opposite force on an opposite side of the piston to move the piston in an opposing direction and, therefore, moving the occluding member away from the means for generating the positive airway pressure.

5. The bi-level positive airway pressure device of claim 3, wherein the means to convert the increase in the gas pressure comprises a diaphragm that seals a chamber into a first section and a second section, the diaphragm mechanically interfaced to the occluding member; the first section fluidly interfaced to the receptor channel and the second section fluidly interfaced to the second receptor channel such that when the exhalation gases flow from the patient port, the increase in the gas pressure in the first section exerts force on a first side of the diaphragm to deform the diaphragm and move the occluding member to block the means for generating the positive airway pressure and when the exhalation gases abate, the increase in the gas pressure in the second section exerts an opposite force on an opposite side of the diaphragm to deform the diaphragm and move the occluding member away from the means for generating the positive airway pressure.

6. The bi-level positive airway pressure device of claim 5, wherein the housing has a taper between the means for generating the positive airway pressure and the patient port, the taper linearly decreases in diameter having a greatest diameter at a point closest to the means for generating the positive airway pressure.

7. A bi-level positive airway pressure device comprising:
- a housing having a patient port for connecting to an airway of a patient;
- a source of positive airway pressure directed through the housing and towards the patient port, the source of the positive airway pressure positioned near an end of the housing that is distal from the patient port;
- a nozzle emitting a jet of a gas directed across the housing at an end of the housing that is closest to the patient port;
- a first receptor positioned on a side of the housing opposite of the nozzle, the first receptor receiving the gas from the jet of the gas when there is absence of exhalation gases flowing from the patient port, thereby an increased gas pressure is present at the first receptor when there is an absence of the exhalation gases flowing from the patient port;
- a second receptor channel positioned on the side of the housing opposite of the nozzle and closer to the source of the positive airway pressure than the first receptor such that the second receptor channel receives the gas from the jet of the gas when the exhalation gases flow from the patient port and through the housing, thereby the increased gas pressure is present in the second receptor channel during exhalation; and
- a diaphragm seals a chamber into a first section and a second section, the diaphragm is mechanically interfaced to an occluding member; the first section of the chamber is fluidly interfaced to the first receptor and the second section of the chamber is fluidly interfaced to the second receptor such that in absence of the flow of the exhalation gases from the patient port, the increase in the gas pressure in the first section exerts force on a first side of the diaphragm to deform the diaphragm and move the occluding member away from the source of the positive airway pressure and when the exhalation gases flow from the patient port, the increase in the gas pressure in the second section exerts an opposing force on an opposite side of the diaphragm to deform the diaphragm and move the occluding member to cover the source of the positive airway pressure.

8. The bi-level positive airway pressure device of claim 7, wherein the diaphragm is connected to the occluding member by a shaft.

9. The bi-level positive airway pressure device of claim 8, wherein the diaphragm and the chamber are located outside of the housing, the occluding member is located within the housing and the shaft passes through the housing.

10. The bi-level positive airway pressure device of claim 9, further comprising a seal around the shaft where the shaft passes through the housing, the seal for preventing the gases from flowing between an area within the housing and a second area within the chamber.

11. A bi-level positive airway pressure device comprising:
- a housing having a patient port for connecting to an airway of a patient;
- a source of positive airway pressure directed through the housing and towards the patient port, the source of the positive airway pressure positioned near an end of the housing that is distal from the patient port;
- a nozzle emitting a jet of a gas directed across the housing at an end of the housing that is closest to the patient port;
- a first receptor positioned on a side of the housing opposite of the nozzle, the first receptor receiving the gas from the jet of the gas when there is absence of exhalation gases flowing from the patient port, thereby an increased gas pressure is present at the first receptor when there is an absence of the exhalation gases flowing from the patient port;
- a second receptor positioned on the side of the housing opposite of the nozzle and closer to the source of the positive airway pressure than the first receptor such that the second receptor receives the gas from the jet of the gas when the exhalation gases flow from the patient port and through the housing, thereby the increase in gas pressure is present in the second receptor during the exhalation; and
- a piston within a cylinder, the piston is mechanically interfaced to an occluding member; a first side of the cylinder is fluidly interfaced to the first receptor and a second side of the cylinder is fluidly interfaced to the second receptor such that in absence of the flow of the exhalation gases from the patient port, the increase in the gas pressure on the first side of the cylinder exerts force on the first side of the piston to move the piston and, therefore, move the occluding member away from source of the positive airway pressure and when the exhalation gases flow from the patient port, the increase in the gas pressure on the second side of the cylinder exerts an opposing force on the second side of the piston to move the piston and, therefore, move the occluding member to block the source of the positive airway pressure.

12. The bi-level positive airway pressure device of claim 11, wherein the piston is connected to the occluding member by a shaft.

13. The bi-level positive airway pressure device of claim 12, wherein the cylinder and the piston are located outside of the housing, the occluding member is located within the housing and the shaft passes through the housing.

14. The bi-level positive airway pressure device of claim 13, further comprising a seal around the shaft where the shaft passes through the housing, the seal for preventing the gases flowing between an area within the housing and an area within the cylinder.

* * * * *